Figure 1:
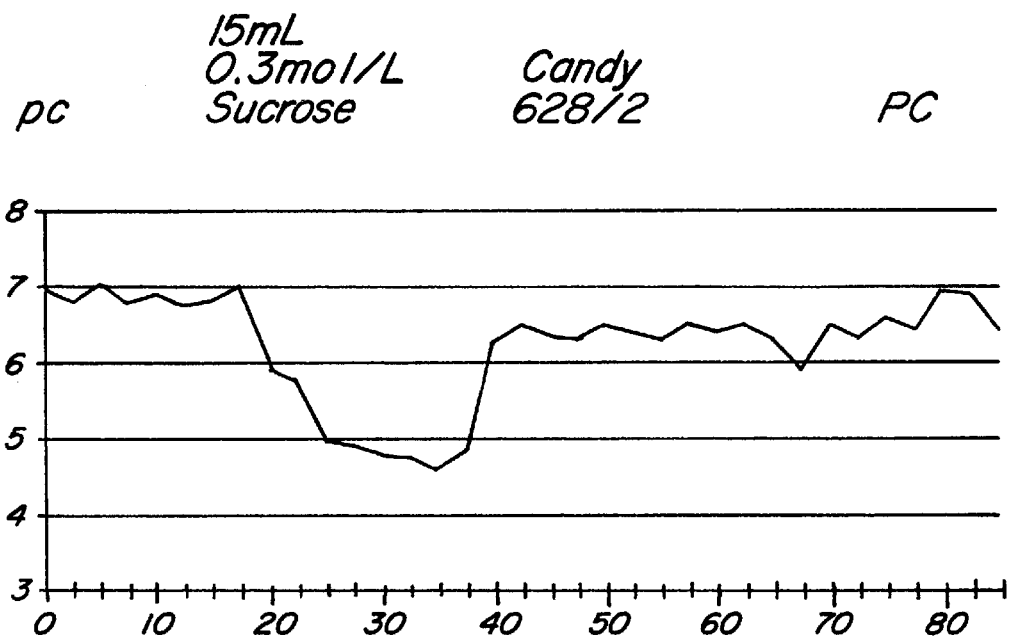

United States Patent

Kaufmann

Patent Number: 5,861,169
Date of Patent: Jan. 19, 1999

[54] HARD CANDY WITH TOOTH PLAQUE-NEUTRALIZING EFFECT COMPRISING AN AMMONIUM SALT

[75] Inventor: Konrad Kaufmann, Dietikon, Switzerland

[73] Assignee: Dibona Holding AG, Zug, Switzerland

[21] Appl. No.: 727,470

[22] PCT Filed: Apr. 7, 1995

[86] PCT No.: PCT/CH95/00078

§ 371 Date: Dec. 20, 1996

§ 102(e) Date: Dec. 20, 1996

[87] PCT Pub. No.: WO95/28910

PCT Pub. Date: Nov. 2, 1995

[30] Foreign Application Priority Data

Apr. 22, 1994 [CH] Switzerland ................ PCT/CH/00078

[51] Int. Cl.⁶ .............. A61K 9/68; A23L 3/34; A23G 3/00
[52] U.S. Cl. .......... 424/440; 426/532; 426/658; 426/660
[58] Field of Search .............. 424/48, 49, 440; 426/3–6, 572, 660, 658, 532

[56] References Cited

U.S. PATENT DOCUMENTS

| | | | |
|---|---|---|---|
| 3,677,770 | 7/1972 | Witzel | 99/134 R |
| 4,048,299 | 9/1977 | Litchfield et al. | 424/49 |
| 4,098,914 | 7/1978 | Knechtel | 426/632 |
| 4,170,632 | 10/1979 | Wagenknecht et al. | 424/48 |
| 4,303,648 | 12/1981 | Witzel et al. | 424/686 |
| 4,409,202 | 10/1983 | Witzel et al. | 424/499 |
| 4,568,537 | 2/1986 | Hoermann et al. | 424/48 |
| 5,185,153 | 2/1993 | Pollock | 424/440 |
| 5,250,569 | 10/1993 | Godfrey | 514/561 |
| 5,312,626 | 5/1994 | Gergely et al. | 424/441 |

OTHER PUBLICATIONS

Derwent Publication Ltd., London, GB; AN 86–011915 & JP–A–60 237 947 (SAN EI CHEM IND KK), 26 Nov. 12985 see abstract and Patent Abstracts of Japan vol. 11 No. 361 (C–459) & JP, A, 62, 132815 (TANAKA KIICHI) 12 Jun. 1987, see abstract, both abstracts are taken from the International Search Report, which also is included herewith.

Patent Abstracts of Japan, vol. 11, No. 361, (C–459) , & JP,A, Jun. 16.

Derwent Publication, AN 86–011915, & JP–A–60 237, Nov. 26.

*Primary Examiner*—Sandra E. Saucier
*Attorney, Agent, or Firm*—Haverstock, Garrett & Roberts

[57] ABSTRACT

A candy is disclosed which neutralizes plaque and contains at least one acid neutralizing substance such as an ammonium salt and may further comprise an alkaline metal salt and an alkaline earth metal salt with sugar substitutes and other ingredients.

9 Claims, 1 Drawing Sheet

HARD CANDY WITH TOOTH PLAQUE-NEUTRALIZING EFFECT COMPRISING AN AMMONIUM SALT

The invention relates to a candy known as a hard candy with tooth plaque-neutralizing effect, the use of a hard candy to clean the teeth, and a process and device for manufacturing a hard candy. The term hard candy is generally understood to mean oval compressed lozenges, chewable candies, pastilles, capsules, tablets, and similar presentations.

After the consumption of food and stimulants, tooth plaque is a particular risk due to the resulting acids. In particular, sugars cause and promote dental caries, and it is currently considered to be scientifically proven that carious lesions are the result of a process that affects hard tooth substances from the outside. The fermentation of orally administered carbohydrates into organic acids in bacterial tooth plaque and the related drop in the pH of that plaque are of primary importance for the formation of caries.

To neutralize tooth plaque acids, alkaline compounds, such as sodium carbonate, bicarbonate, and ammonium phosphate, as well as ureas, are recommended to counter the organic acids that are formed by the fermentation of carbohydrates. However, the salty and sometimes bitter taste of those buffers has made it difficult to use them.

The most effective mechanical method of inhibiting caries is to clean the teeth with toothpaste and a toothbrush after every occasion on which stimulants or food are consumed. However, it is not always possible to clean the teeth with toothpaste and a brush after every meal or every time food is consumed. That is particularly the case when away from home, traveling, at work, and the like.

EP-525 388 describes the manufacture and composition of a tablet having the aim of producing a slight foaming action to improve the taste of tablets containing active pharmaceutical ingredients, particularly calcium and magnesium. U.S. Pat. No. 4,409,202 describes a tablet or candy whose aim is to cover or neutralize mouth odor. The main active ingredient is a vegetable oil. U.S. Pat. No. 5,250,569 proposes the use of amino acids, including in connection with toothpastes, to avoid the unpleasant taste of orally-administered aluminum compounds. It would then be possible to produce special rhinitis medications containing aluminum. Another aim of that U.S. patent is to produce a slow-release effect for aluminum. The aim of JP-A-60237947 is the proprietary manufacture of a specific appearance for candy. A special look for the final product can be obtained by enclosing air bubbles, which are obviously intended to give the candy a refreshing effect. Finally, JP-A-62132815 suggests the manufacture of tablets to clean the mouth and deodorize the breath. However, both the state-of-the-art and proposed measures are not appropriate for effectively inhibiting caries.

Against that background, so-called plaque-neutralizing chewing gums have been available for some time that are intended both to stimulate the flow of saliva as a result of chewing movements and to contain the aforementioned active ingredients, which cause a buffer action in the saliva or result in neutralization of the acids produced during the fermentation of carbohydrates. Those chewing gums have the advantage that they can be used immediately after eating and can at least to a great extent neutralize the acids that damage the teeth. That may be done by stimulating the flow of saliva, whereby an increased buffer capacity is produced, by promoting the neutralization of plaque acids, by increasing the distribution of saliva in difficult to reach interdental spaces, by improved removal of food particles from the oral cavity, by creating a pH value that promotes remineralization of the tooth enamel, or finally by promoting remineralization by stimulating the flow of saliva with an increased mineral content.

Such chewing gums are also useful, for example, for patients with temporary or chronically limited mobility, which generally leads to poorer oral hygiene. In addition, when taking medications that inhibit the flow of saliva, the aforementioned chewing gum can be a useful tool for improving oral hygiene.

However, the problem with such plaque-neutralizing chewing gums is that gum chewing is socially unacceptable to many people, or is rejected for other reasons, for example in the presence of dental prostheses, synthetic teeth, and the like. Therefore, one aim of the present invention is to create an alternative to chewing gum that increases neutralization of acid plaque, thereby preventing or at least inhibiting formation of caries in the presence of plaque.

The stated aim is achieved in accordance with the invention by means of a hard candy in accordance with the wording of claim 1.

A hard candy with plaque-neutralizing effect is suggested that contains at least one active ingredient that neutralizes acid to a great extent, as known for example from the aforementioned chewing gums.

The advantage of the hard candy in accordance with the invention is, on the one hand, that the problems described in connection with chewing gums are eliminated. In addition, it is known that when chewing gum is used, the active ingredients that it contains are released by strong chewing during the first 1–2 minutes, and that very few other effective neutralizing substances are released by the chewing gum after about two minutes, which naturally reduces the neutralizing effect. In contrast, a hard candy better distributes the dose of neutralizing active ingredient and can last up to 5–6 minutes. Moreover, the stimulation of saliva flow is nearly identical to that when chewing gum is used.

The suggested active ingredients are ammonium salts, alkaline metal salts, and alkaline earth metal salts, in particular phosphates, carbonates, hydrocarbonates, and hydrogen phosphates, as well as urea or urea peroxide.

To cover the occasionally salty, soapy, or bitter taste of those acid-neutralizing active ingredients, sugar substitutes or sugar replacements and sweeteners are preferably added to the hard candy in accordance with the invention. In that regard, examples include isomalt, sorbitol, acesulfam, lycasine, sweeteners containing cyclamate, aspartame, etc.

Moreover, it has proven beneficial to add xylitol as an addition to the acid-neutralizing active ingredient, because xylitol also has a certain inhibiting effect on plaque formation, particularly in conjunction with the aforementioned active ingredient.

In addition to the aforementioned substances or active ingredients, the hard candies in accordance with the invention contain at least one carrier, as well as one or more taste-imparting flavoring agents, such as peppermint flavor, orange flavor, and the like.

The proportion of acid-neutralizing active ingredients in the hard candy in accordance with the invention should be at least 0.1 percent by weight, preferably between 0.2 and 15 percent by weight, based on the total weight of the hard candy. However, in practice it has been shown that the proportion of acid-neutralizing active ingredients should be between 0.5 and 3 percent by weight, preferably from 1 to 2.5 percent by weight, because otherwise it becomes difficult to "neutralize" the bitter, salty, or soapy taste.

In accordance with a preferred variation of the hard candy in accordance with the invention, the use of diammonium hydrogen phosphate and sodium hydrocarbonate or a mixture of the two as an acid-neutralizing active ingredient is suggested.

It is fundamentally a new idea to use a hard candy to neutralize tooth plaque or to provide a hard candy with a neutralizing active ingredient.

To manufacture a hard candy in accordance with the invention, it is suggested to use a fundamentally known process for manufacturing candy, although it is suggested to select a temperature that does not exceed 135° C. during the metered addition of the acid-neutralizing active ingredients to the candy manufacturing mass. It has been shown in practice that in general the active substances that are essential to the invention at least partially decompose or are broken down at temperatures higher than the specified level of 135° C.

For that reason, in accordance with the invention a device or equipment for manufacturing a hard candy is suggested that is fundamentally based on a device or equipment usually used for manufacturing hard candies. It is essential to the invention that subsequent to the cooking vessel, such as for example a cooking coil, where the various basic materials, such as carriers, water, sugar substitutes, and the like are cooked and mixed at approximately 160° C., the mass is cooled by an additional cooler to a temperature from approximately 130°–135° C. The proposed additional cooler is generally not included in such equipment. The metered addition of the acid-neutralizing active ingredients occurs after said additional cooling, as suggested above.

Additional preferred characteristics of the invention are set forth in dependent claims 2 through 8.

The invention will now be explained in greater detail below using an example, whereby experiments in which the neutralizing candy in accordance with the invention was given to a series of test subjects at the Dental Institute of the University of Zurich confirmed the neutralizing effect of candy. The results obtained by the Dental Institute of the University of Zurich are explained in greater detail or confirmed by the attached Figures, in which:

A BRIEF DESCRIPTION OF THE DRAWINGS

Figure 2:
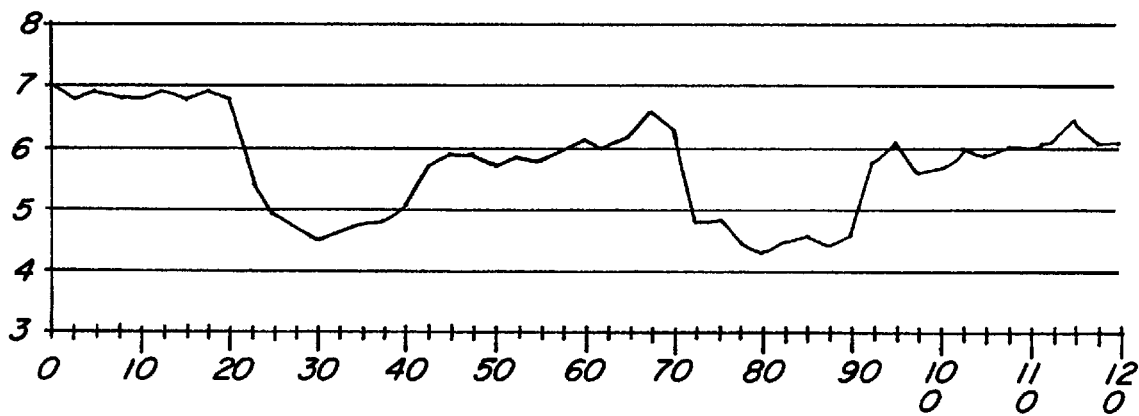

FIG. 1 shows the neutralizing effect of a candy on interdental plaque that has been acidified by sucrose fermentation and FIG. 2 compares the neutralizing effect of a hard candy in accordance with the invention or neutralizing candy and a known tooth cleaning chewing gum The applicant for the present invention retained the Division of Preventive Dentistry, Periodontology and Caries of the Dental Institute of the University of Zurich to perform various tests on a sample of the described neutralizing candy in accordance with the invention to determine its tooth-protecting characteristics and its plaque-neutralizing effect.

The recipe for the neutralizing candy that was used contained the following ingredients:

Recipe for Neutralizing Candy

| Raw materials | Weighed portion in kg | Weighed portion in end product with approx. 99% dry substance | Weighed portion in 100 g/% candy at 1.8 g |
|---|---|---|---|
| Water | 183.8333 | 10.1238 | 1.000 |
| Sugar substitutes: | | | |
| Isomalt 95% | 1,038.1686 | 986.2583 | 97.4195 |
| Xylitol CM 100% | 6.5000 | 6.5000 | 0.6420 |
| Diammonium hydrogen phosphate | 4.0000 | 4.0000 | 0.3951 |
| Sodium hydrocarbonate | 2.5000 | 2.5000 | 0.2469 |
| Peppermint flavor | 2.0000 | 2.0000 | 0.1975 |
| Acesulfam K | 1.0000 | 1.0000 | 0.0987 |
| (no breakdown) | 1,237.9999 | 1,012.3821 | 99.9997 |

The tests were done on eight test subjects in excellent health. They had already participated in previous tests, and the physiological conditions in their oral cavities were known in detail to the researchers. Average values for the individual plaque pH curves of the test subjects after 10% sucrose rinsing obtained over several years are stored for comparison in the computer database of the Dental Institute. All test subjects had a lower jaw telemetric prosthesis with one miniature pH glass electrode installed in an interproximal space.

The test prostheses were cleaned and inserted and the test subjects were instructed to continue with their normal eating habits during the test but to refrain from any oral hygiene on the lower jaw. They were allowed to rinse with water to remove food particles and to use a toothbrush without toothpaste on the upper jaw. Not removing the prostheses allowed undisrupted growth of plaque on the membrane surfaces of the interdentally installed electrodes. The following two test sequences were then used, and the pH values were obtained during the following two test sequences, while 0.3 mol/L 10% sucrose rinse solution or candy containing sugar were used as positive controls.

| | minutes |
|---|---|
| Test sequence 1 FIG. 1 | |
| Chew paraffin | 3 |
| Rest period | 4 |
| Monitoring period | 15 |
| 15 ml. 0.3 mol/L sucrose rinse | 2 |
| Monitoring period | 15 |
| Suck on a 628/2 candy | individual |
| Monitoring period | 30 |
| Water rinse | 2 |
| Chew paraffin | 3 |
| Rest period | 4 |
| Test sequence 2 FIG. 2 | |
| Chew paraffin | 3 |
| Rest period | 4 |
| Monitoring period | 15 |
| 15 ml. 0.3 mol/L sucrose rinse | 2 |
| Monitoring period | 15 |
| Suck on a 628/2 candy | individual |
| Monitoring period | 15 |

-continued

|  | minutes |
| --- | --- |
| Water rinse | 2 |
| Chew paraffin | 3 |
| Rest period | 4 |
| 15 ml. 0.3 mol/L sucrose rinse | 2 |
| Monitoring period | 15 |
| Chew Candida chewing gum | as for candy |
| Monitoring period | 15 |
| Water rinse | 2 |
| Chew paraffin | 3 |
| Rest period | 4 |

Test sequence 1 was performed to determine the plaque-neutralizing effect and test sequence 2 was performed to compare the plaque-neutralizing effect of candy in accordance with the invention with the effect of a neutralizing chewing gum. Test sequence 1 is graphically illustrated in FIG. 1, while test sequence 2 is graphically illustrated in FIG. 2. It should be noted that a corresponding diagram was of course prepared for each one of the eight test subjects, but to represent them only one is shown in both FIGS. 1 and 2.

The test results shown in FIGS. 1 and 2 indicate that the buffering food additives added to the candy in accordance with the invention are capable of quickly neutralizing acidified plaque caused by carbohydrate fermentation subsequent to a sucrose rinse, thereby limiting the harmful effect of the sucrose. In addition, FIG. 2 compares the plaque-neutralizing effect of the tested candy with that of a state-of-the-art chewing gum, brand name Candida. Although chewing gum can cause a higher saliva flow rate due to mechanical stimulation (chewing movement), the candy can achieve the same effect thanks to the buffer substances that it contains.

Of course, the recipe set forth above for manufacturing a hard candy or neutralizing candy in accordance with the invention is only an example for the purpose of providing a more detailed explanation of the invention and so that tests could be done using a formulation in accordance with the invention. Obviously the formulation can be changed, varied, or added to in accordance with the measures set forth in the claims. It is fundamentally surprising that a hard candy that has a neutralizing or cleansing effect can be used to achieve practically the same result as is obtained using the aforementioned chewing gum. Because the acceptance of using a hard candy is significantly higher than is the case for chewing gum, a solution is offered for neutralizing the acids formed in the oral cavity after partaking of food or stimulants, at least in special situations or when special conditions prevail. Of course, a hard candy in accordance with the invention cannot replace the ultimate cleaning of the teeth using a toothbrush.

I claim:

1. A candy composition for plaque neutralization, wherein said candy composition comprises an acid neutralizing active ingredient and at least one sugar substitute, wherein said acid neutralizing active ingredient is:

an ammonium salt.

2. The candy composition of claim 1, wherein said candy composition further comprises xylitol.

3. The candy composition of claim 1, wherein said candy composition further comprises at least one carrier and at least one taste imparting flavoring agent.

4. The candy composition of claim 1, wherein said acid neutralizing active ingredient is at least 0.1 percent by weight, based on the total weight of said candy composition.

5. The candy composition of claim 4, wherein said acid neutralizing active ingredient is from 1 to 2.5 percent by weight, based on the total weight of the candy composition.

6. The candy composition of claim 1, wherein said candy composition further comprises a sweetener.

7. The candy composition of claim 1, further comprising an alkaline metal salt and an alkaline earth metal salt.

8. A method for making a plaque neutralizing candy comprised of an acid neutralizing active ingredient, wherein the steps for making said candy include:

(a) mixing together carriers, water, and sugar substitutes;

(b) heating the mixture of the carriers, water, and sugar substitutes to 80° C.;

(c) cooking the mixture of the carriers, water, and sugar substitutes at a temperature over 160° C.;

(d) cooling the cooked mixture by transferring the mixture to an additionally provided cooler and cooling the mixture to a temperature lower than 135° C., so that during a subsequent metered addition of xylitol and an acid neutralizing active ingredient which is diammonium hydrogen phosphate, the acid neutralizing ingredient does not decompose due to an excessively high temperature of the mass;

(e) adding an amount of the acid neutralizing active ingredient and xylitol to the mixture cooled below 135° C.; and, (f) shaping the cooled mass containing the acid neutralizing active ingredient into candy.

9. A candy composition for use in plaque neutralization, wherein said candy composition is comprised of:

(a) an acid neutralizing active ingredient, wherein said acid neutralizing active ingredient is an ammonium salt;

(b) at least one carrier;

(c) xylitol;

(d) at least one taste imparting flavoring agent; and, (e) at least one sugar substitute, wherein said candy composition can be used to neutralize plaque.

\* \* \* \* \*

UNITED STATES PATENT AND TRADEMARK OFFICE
CERTIFICATE OF CORRECTION

PATENT NO. : 5,861,169
DATED : January 19, 1999
INVENTOR(S) : Konrad Kaufmann

It is certified that error appears in the above-identified patent and that said Letters Patent is hereby corrected as shown below:

On the front page, the Foreign Application Priority Data is listed incorrect, "PCT/CH/00078" should be --1251/94-0 --.

Signed and Sealed this

Eighth Day of June, 1999

*Attest:*

Q. TODD DICKINSON

*Attesting Officer*      *Acting Commissioner of Patents and Trademarks*